US011959841B2

(12) United States Patent
McGrath et al.

(10) Patent No.: US 11,959,841 B2
(45) Date of Patent: Apr. 16, 2024

(54) DEVICE AND METHOD FOR ISOLATING EXTRACELLULAR VESICLES FROM BIOFLUIDS

(71) Applicant: University of Rochester, Rochester, NY (US)

(72) Inventors: James Lionel McGrath, Rochester, NY (US); Kilean Scott Lucas, Bozeman, MT (US); Henry Hung Li Chung, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 318 days.

(21) Appl. No.: 16/476,329

(22) PCT Filed: Jan. 8, 2018

(86) PCT No.: PCT/US2018/012735
§ 371 (c)(1),
(2) Date: Jul. 8, 2019

(87) PCT Pub. No.: WO2018/129429
PCT Pub. Date: Jul. 12, 2018

(65) Prior Publication Data
US 2021/0356366 A1 Nov. 18, 2021

Related U.S. Application Data

(60) Provisional application No. 62/443,749, filed on Jan. 8, 2017.

(51) Int. Cl.
*G01N 1/40* (2006.01)
*B01D 69/02* (2006.01)
(Continued)

(52) U.S. Cl.
CPC .......... *G01N 1/4005* (2013.01); *B01D 69/02* (2013.01); *B01D 71/02* (2013.01); *B01D 71/52* (2013.01);
(Continued)

(58) Field of Classification Search
CPC .... B01D 39/2068; B01D 71/02; B01D 61/18; B01D 2325/022; B01D 2315/10; B01D 2321/04; G01N 1/4005; G01N 2001/4016
See application file for complete search history.

(56) References Cited

U.S. PATENT DOCUMENTS

| 2008/0179243 | A1* | 7/2008 | Hirsh | B01J 20/287 |
| | | | | 210/635 |
| 2009/0131858 | A1* | 5/2009 | Fissell | B01D 67/0034 |
| | | | | 210/243 |
| 2014/0353231 | A1* | 12/2014 | Arechiga | B01D 63/066 |
| | | | | 427/230 |

OTHER PUBLICATIONS

Li et al. (Langmuir, 2016, 32, p. 11386-11394). "Vapor-Phase Carbenylation of Hard and Soft Material Interfaces" (Year: 2016).*
(Continued)

*Primary Examiner* — Ryan B Huang
(74) *Attorney, Agent, or Firm* — Patent Technologies, LLC; Robert D. Gunderman, Jr.

(57) ABSTRACT

A device and method for isolating extracellular vesicles from biofluids is disclosed. A nanoporous silicon nitride membrane is provided with a tangential flow of biofluid. A pressure gradient through the nanoporous silicon nitride membrane facilitates capture of extracellular vesicles from the tangential flow vector of biofluid. Reversal of the pressure gradient results in the release of the extracellular vesicles for subsequent collection.

35 Claims, 11 Drawing Sheets

(51) Int. Cl.
*B01D 71/02* (2006.01)
*B01D 71/52* (2006.01)
*C12N 15/10* (2006.01)

(52) U.S. Cl.
CPC .... *C12N 15/1017* (2013.01); *B01D 2325/027* (2013.01); *B01D 2325/42* (2013.01); *G01N 2001/4016* (2013.01)

(56) References Cited

OTHER PUBLICATIONS

Stine et al. (Langmuir 2007, 23, p. 4400-4404). "Formation of Primary Amines on Silicon Nitride Surfaces: a Direct, Plasma-Based Pathway to Functionalization" (Year: 2007).*
Vlassiouk et al. (PNAS, 106, 50, Dec. 15, 2009; p. 21039-21044). "Versatile ultrathin nanoporous silicon nitride membranes" (Year: 2009).*

* cited by examiner

DEVICE AND METHOD FOR ISOLATING EXTRACELLULAR VESICLES FROM BIOFLUIDS

CROSS REFERENCE TO RELATED PATENT APPLICATIONS

This application claims priority to U.S. patent application Ser. No. 62/443,749 filed Jan. 8, 2017 entitled "Device and Method for Isolating Extracellular Vesicles From Biofluids" by Dr. James L. McGrath et al., and to International Application Number PCT/US18/12735 filed Jan. 8, 2018 entitled "Device and Method for Isolating Extracellular Vesicles From Biofluids", the entire disclosures of which are incorporated herein by reference in their entirety.

STATEMENT REGARDING FEDERALLY SPONSORED RESEARCH OR DEVELOPMENT

This invention was made with government support under 1521373 awarded by National Science Foundation. The government has certain rights in the invention.

BACKGROUND OF THE INVENTION

1. Field of the Invention

The present invention relates generally to fluid separation, and more particularly to a device and related method for separating extracellular vesicles from biofluids.

2. Description of Related Art

Extracellular vesicles, once thought to be simply membrane debris with no biological value, are now understood to play a vital role in cell to cell communication within multi-cellular organisms.

Extracellular vesicles are lipid bilayer particles derived from several cellular pathways including exosomes, microvesicles, and apoptotic bodies. Exosomes of 30-100 nm diameter are derived from the endosomal pathway. Microvesicles of 100 nm-1 um diameter are derived from the plasma membrane. Extracellular vesicles can be found in biofluids such as blood, plasma, serum, urine, cerebrospinal fluid, aqueous humor, lymph, breast milk, semen, and conditioned cell culture media, among others.

It is now known that extracellular vesicles have significance in normal physiological processes including tissue regrowth and repair, immunological responses, coagulation of blood, and also in the pathological progress of many diseases. As such, they represent tremendous possibilities for therapeutic applications. The applications for extracellular vesicles are growing in diversity and significance for both normal and pathological processes. Identifying specific EV markers offers tremendous potential for new therapeutic targets, as well as for liquid biopsy prognostics and for companion diagnostics to monitor treatment response. Extracellular vesicles also can transport nucleic acids during cell to cell communication, and thus represent tremendous potential for drug delivery vehicles. Extracellular vesicles also hold equally tremendous potential as therapeutics in regenerative medicine, as vaccination agents and as delivery agents by way of using their innate ability to transmit various RNA species among cells.

While the uses for extracellular vesicles continues to increase both in research and in direct and indirect therapeutic applications, isolating extracellular vesicles from bodily fluids remains a difficult and slow process. Techniques such as ultrafiltration and gelation result in significant contamination from protein and complex and tedious secondary processes to eliminate the protein contamination from the desired extracellular vesicles.

What is therefore needed is a device that captures the majority of extracellular vesicles in a bodily fluid while avoiding protein contamination. What is also needed is a device that is reusable and relatively fast in capturing and retaining extracellular vesicles in a bodily fluid.

BRIEF SUMMARY OF THE INVENTION

In accordance with the present invention, there is provided a device and method for isolating extracellular vesicles from biofluids. A nanoporous silicon nitride membrane is provided and receives a tangential flow of biofluid. A pressure gradient through the nanoporous silicon nitride membrane facilitates capture of extracellular vesicles from the tangential flow vector of biofluid. Reversal of the pressure gradient results in the release of the extracellular vesicles for subsequent collection. Defined surface chemistries of the nanoporous silicon nitride membrane may also be employed to augment capture and subsequent collection of these extracellular vesicles.

The foregoing has been provided by way of introduction, and is not intended to limit the scope of the invention as described by this specification, claims and the attached drawings.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims and drawings attached hereto.

DESCRIPTION OF THE PREFERRED EMBODIMENTS

The present invention involves the capture and physical retention and sieving of extracellular vesicles from biofluids. A device and method for isolating extracellular vesicles from biofluids is thus described, with various embodiments also described and envisioned herein.

The present invention makes use of nanoporous silicon nitride membranes in a tangential flow device, wherein the extracellular vesicles are captured by a novel, diffusion-driven, physical sieving mechanism, allowing for subsequent isolation and purification thereof.

In use, a biofluid is slowly passed over the nanoporous silicon nitride membrane under conditions of slight negative transmembrane pressure. This configuration permits the diffusion of extracellular vesicles toward the nanoporous membrane, such that the extracellular vesicles are captured in the pores of the membrane. While maintaining a negative transmembrane pressure, the extracellular vesicles can be retained in the pores while the fluid component of the biofluid is swept and cleared away, thus removing unwanted constituents from the biofluid. While maintaining transmembrane pressure, the captured extracellular vesicles can be washed in a clean solution to increase their purity. Finally, the transmembrane pressure can be released or reversed to slightly positive and the isolated extracellular vesicles are eluted off the membrane in a bolus of clean solution.

Surprisingly, extracellular vesicles are captured under native conditions using the present invention. Other methods require addition of buffers and/or salts to manipulate the pH or ionic strength of the biofluid in order to absorb the extracellular vesicles onto a filtration media for their isolation.

The physical sieving mechanism described herein where the extracellular vesicles are captured on the pores of the nanoporous silicon nitride membrane by diffusion into the slight transmembrane pressure environment of the porous membrane, in the context of a tangential flow configuration of the present invention, seems to depend on an excess of pores relative to the number of extracellular vesicles in the biofluid. Thus, a large pore-to-extracellular vesicle ratio is required for the isolation mechanism of the present invention and will likely only work with highly permeable membranes with a large density of pores (e.g., ~; $10^7$ pores per $mm^2$).

The tangential flow configuration described herein results in the apparent removal of the unwanted but highly abundant species within most biofluids, with little residual contamination. For example, the high protein content of plasma can be removed from captured extracellular vesicles so that a highly pure extracellular vesicle preparation is realized.

For a more thorough understanding of the present invention and the various embodiments described and envisioned herein, reference is now made to the Figures.

Figure 1:
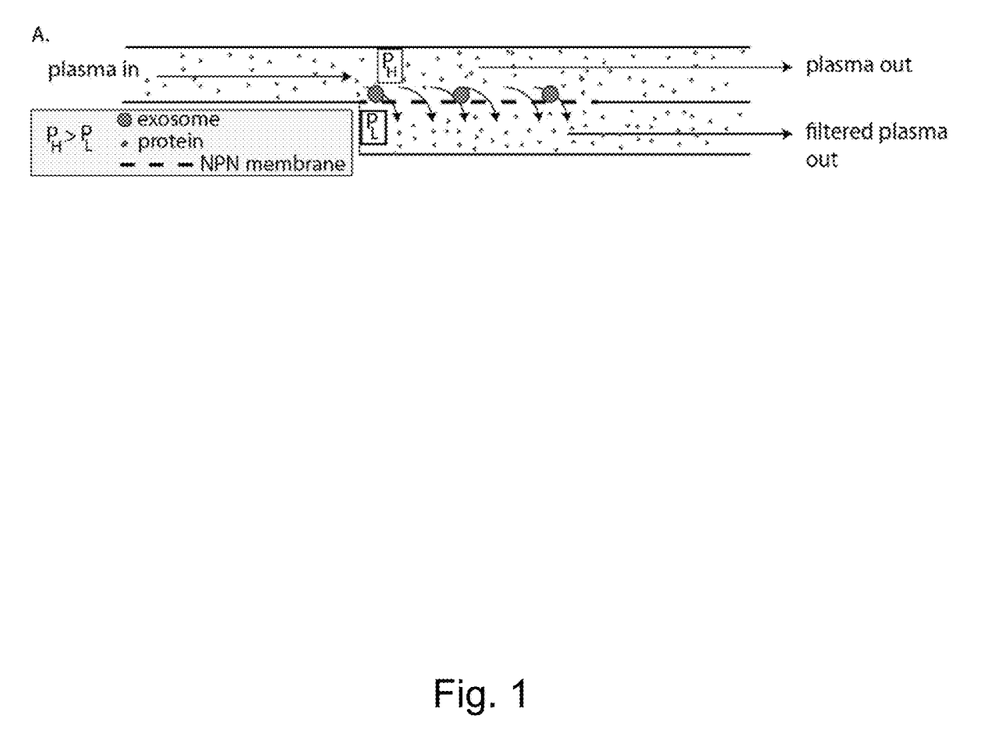
FIG. 1 depicts capture of exosomes on a tangential flow device of the present invention.

FIG. 1 depicts capture of exosomes on a tangential flow device of the present invention. A tangential fluid flow device for creating a tangential fluid flow velocity of a biofluid across the surface of the nanoporous membrane may include a conduit, a vessel, a channel, a tube, or any structure capable of retaining a fluid under flow conditions. The tangential fluid flow in turn may be created using a pump, gravity, electrostatic forces, thermal or chemical gradients, or the like. The vector labeled "plasma in" illustrates tangential flow across a nanoporous silicon nitride (NPN) membrane where a pressure gradient exists, providing a slightly lower pressure below the membrane than above the membrane, which pulls extracellular vesicles such as exosomes into the pores of the NPN membrane as protein is cleared. A pressure gradient from one side of the nanoporous membrane to the other side (through the nanoporous membrane) may be created with a pressure gradient device such as a pump, a diaphragm, a vacuum device, a thermoelectric device such as a peltier device, a mechanical device for fluid flow modification, or the like. Further, a device for reversing the created pressure gradient is provided, and may include a pump controller for changing the direction of pump rotation, a switch for changing polarity or removing electrical power from a thermoelectric device, a valve or fluid diversion structure, a vacuum controller for changing or removing vacuum from one side of the membrane, or the like. As labeled in FIG. 1, the extracellular vesicles are diagrammatically depicted as shaded circles and protein is diagrammatically depicted as a distorted asterisk of sorts. The dotted line depicts the surface of the NPN membrane. Such a membrane is described, for example, in United States Patent application publication 2016/0199787 A1 to Striemer et al. and entitled Nanoporous Silicon Nitride Membranes, And Methods For Making And Using Such Membranes, the entire disclosure of which is incorporated herein by reference. Other membranes, devices and methods applicable to the present invention and the various embodiments described, depicted and envisioned herein are disclosed in U.S. Pat. Nos. 8,518,276 and 8,501,668, the entire disclosures of which are incorporated herein by reference in their entirety. Once the extracellular vesicles are captured through the process depicted and described by way of FIG. 1, a cleanup stage occurs as depicted in FIG. 2.

For exosome capture in the tangential flow device of the present invention, in a preferred embodiment, transmembrane pressure in operation will be 1 pascal-1 atmosphere. Flow velocity will be 10 μm/sec.-10 cm./sec. Channel length will be 1 mm.-1 m. along the principal direction of flow. A large channel size may be used, for example in a large industrial size operation. Roll to roll processing, for example, could be used to create sheets of nanoporous silicon nitride (NPN). Channel height will be 100 nm.-1 mm. Pore diameter will be 20 nm.-35 nm., or in some embodiments of the present invention, 20 nm.-80 nm., or up to 120 nm. The membranes in some embodiments may be as thin as 30 nm.

Figure 2:
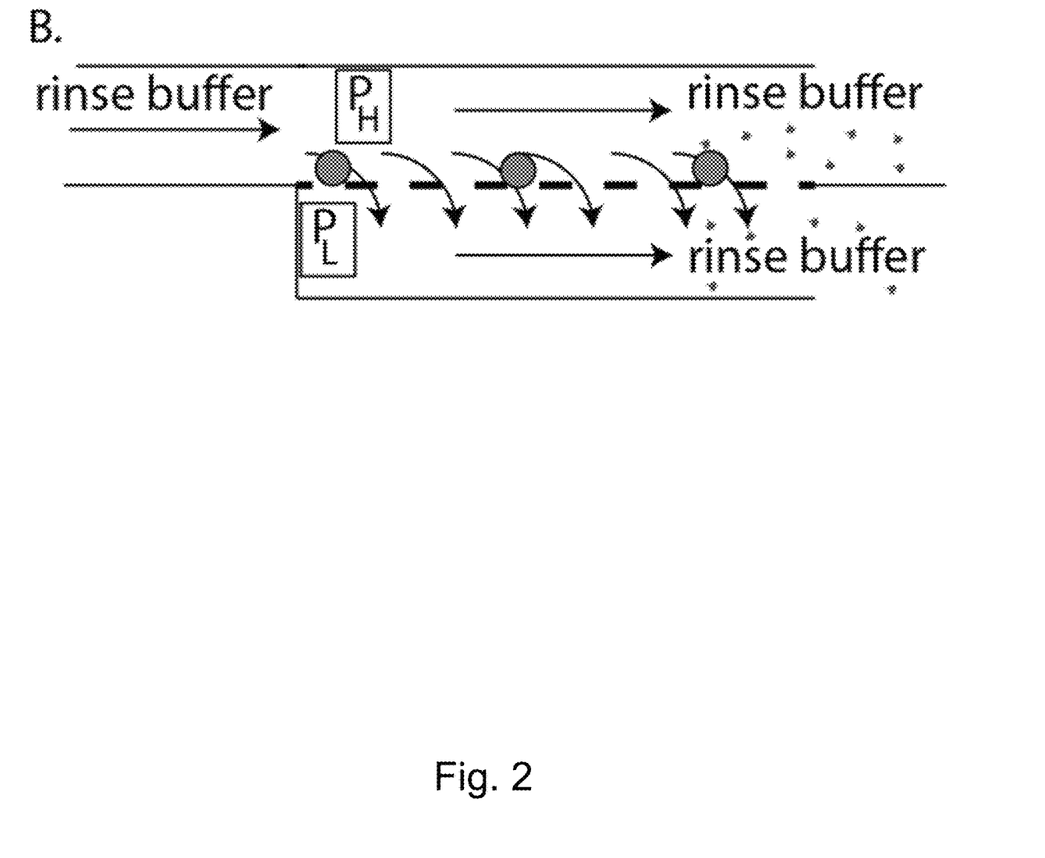
FIG. 2 depicts clearing of protein contaminants on the tangential flow device of FIG. 1.
Figure 3:
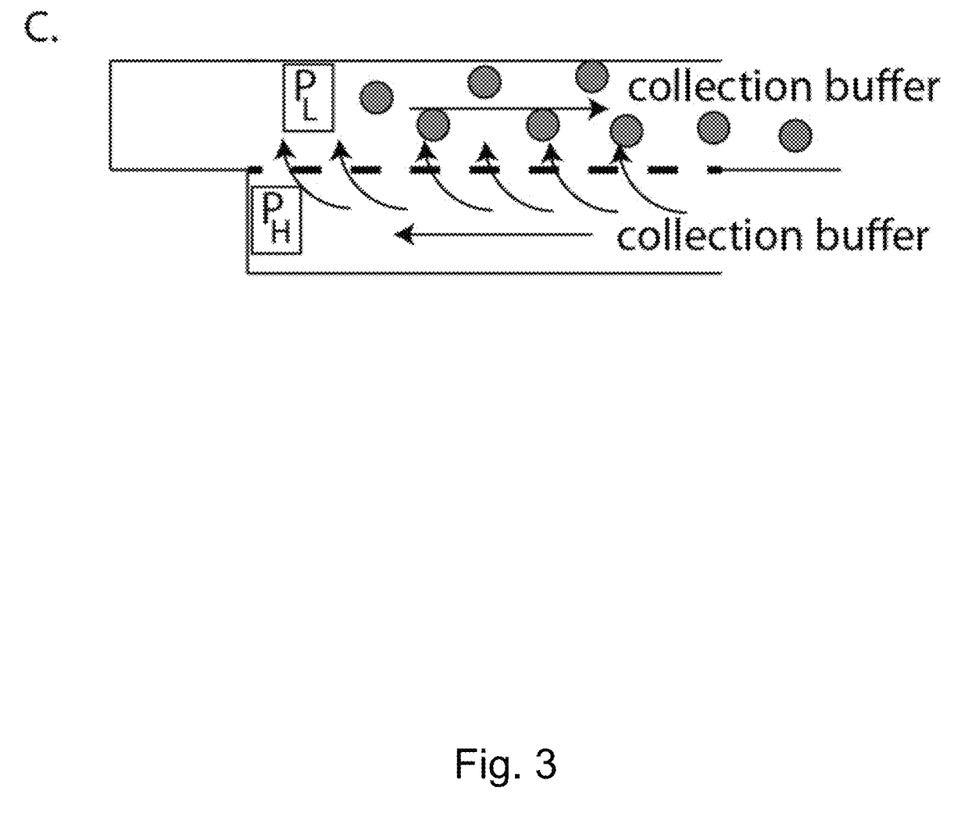
FIG. 3 depicts collection of exosomes using transmembrane pressure reversal of the device of FIG. 1.

FIG. 2 depicts clearing of protein contaminants on the device of the present invention. Once the extracellular vesicles are extracted from the plasma, a buffer solution is passed through the system to clear protein contaminants, leaving behind extracellular vesicles entrapped or otherwise captured in the nanoporous silicon nitride (NPN) membrane. The next step, as described in FIG. 3, involves the collection of the entrapped extracellular vesicles using transmembrane pressure reversal such that the pressure gradient from one side of the nanoporous silicon nitride (NPN) membrane is reversed to then allow for the collection of the extracellular vesicles in a controlled volume. The area of the silicon nitride membrane (NPN) can be varied to change the quantity of extracellular vesicles collected in each pass or cycle of plasma flow, buffer rinse and pressure reversal. One can envision such a cycle to be repeated many times over in proportion to plasma flow and quantity.

Figure 4:
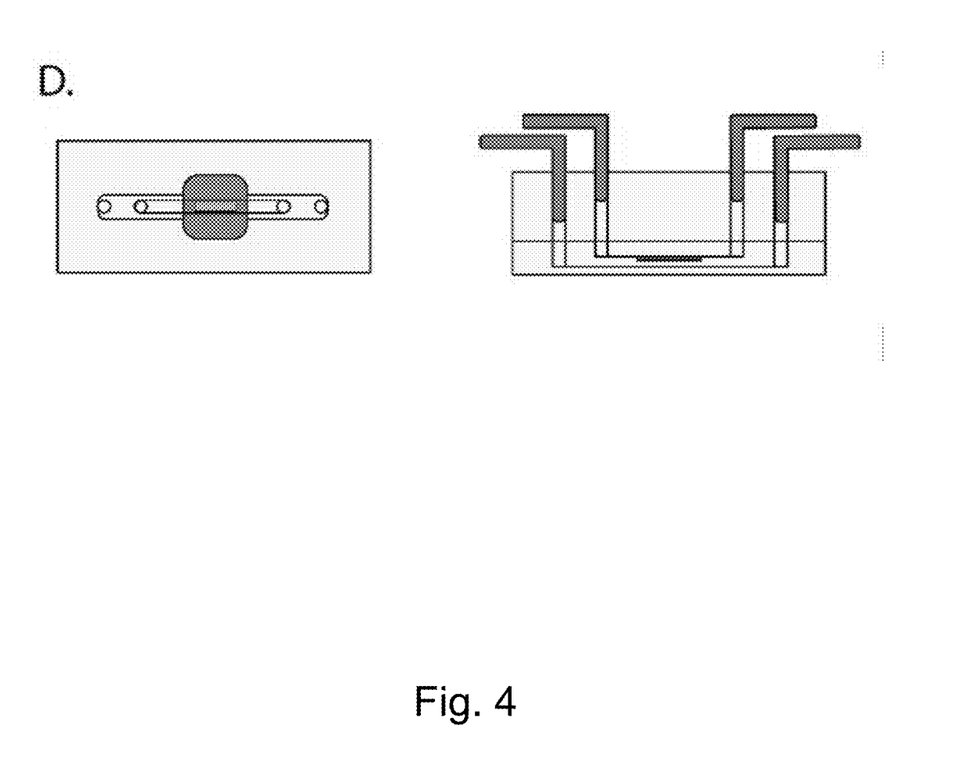
FIG. 4 is a schematic diagram of a microfluidic chip based device of the present invention.

Packaging of the device may include industrial or laboratory scale setups, or may, in some embodiments of the present invention, include chip based packaging. For example, FIG. 4 is a schematic diagram of a microfluidic chip based device of the present invention. Microfluidic access at the inlet and outlet of the top and bottom chambers can be seen.

Figure 5:
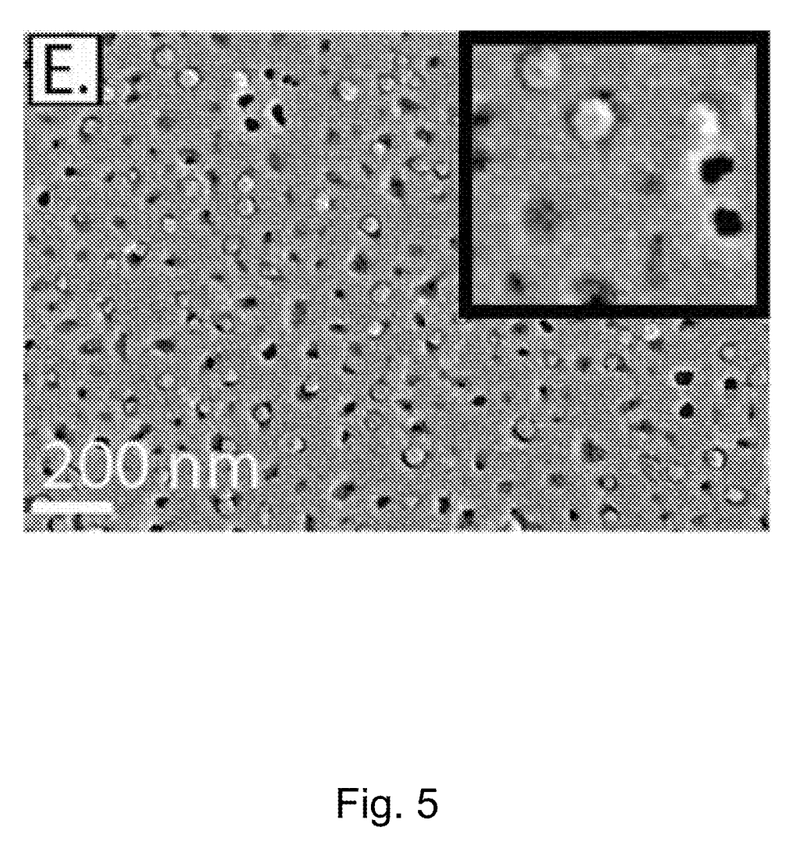
FIG. 5 shows exosome capture from pure plasma on nanoporous silicon nitride.

FIG. 5 shows exosome capture from pure plasma on nanoporous silicon nitride where extracellular vesicles are trapped in NPN pores. The inset in FIG. 5 depicts captured extracellular vesicles adjacent to open pores in the NPN membrane.

There may be a variety of pore geometries employed. For example, a "bowl with a hole structure where the side of the pore facing the tangential flow of the material to be processed has a wide mouth and the back side has a smaller hole than the side facing the tangential flow. This geometry allows the liquid to drain through the smaller hole while preventing escape of the exosome in the tangential flow. Such a geometry maximizes the range of exosome capture while still allowing transmembrane flow. In other words, while the nanoporous membrane comprises a first surface having a plurality of pores that are exposed to the tangential flow of material, the nanoporous membrane further comprises a second surface where the plurality of pores from the first surface extend through the second surface and where the plurality of pores of the first surface are of a greater diameter than the related plurality of pores that extend through the second surface.

Figure 6:
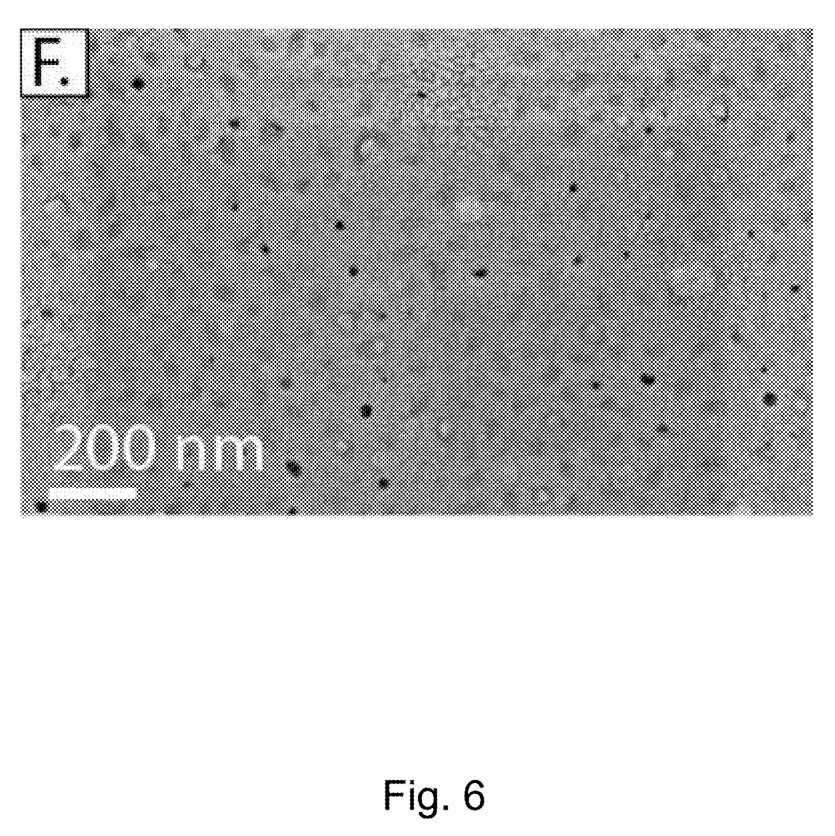
FIG. 6 shows isolation of a sample prepared with a reagent and associated membrane clogging.

FIG. 6 shows isolation of a sample prepared with Exoquick™ reagent and associated membrane clogging. The contamination of the NPN membrane by the ExoQuick™ polymer is evident from the texture and electron beam charging effects (shading). Note also that fewer exosomes are seen in the image and many pores appear clogged. The ability of NPN to purify extracellular vesicles such as exosomes directly from raw biofluids like plasma promises both a simpler and cleaner preparation of exosomes.

Examples of devices according to the present invention that can perform extracellular vesicle isolation as described herein include microfluidic format devices.

By way of example, and not limitation, one can envision a two-channel configuration with the semi-permeable nanoporous membrane fluidically connecting the two flow channels. In this embodiment, the nanoporous membrane could be nanoporous silicon nitride (NPN) with ~30 nm diameter pores. This membrane would permit the capture of exosomes that are 30-100 nm diameter. Such material is described, for example, in PCT/US2014/1051316, the entire disclosure of which is incorporated herein by reference.

In another embodiment, a second semi-permeable membrane, with 100, 200 or 1,000 nm diameter pores is placed upstream of the first 30 nm diameter pore membrane and fluidically connected so that extracellular vesicles smaller than the pores of the first membrane permeate to the second membrane with ~30 nm pores. This would permit size fractionation of a biofluid's extracellular vesicles into micro vesicle (>100 nm but <1.000 nm) and exosome (30-100 nm) fractions.

Figure 7:
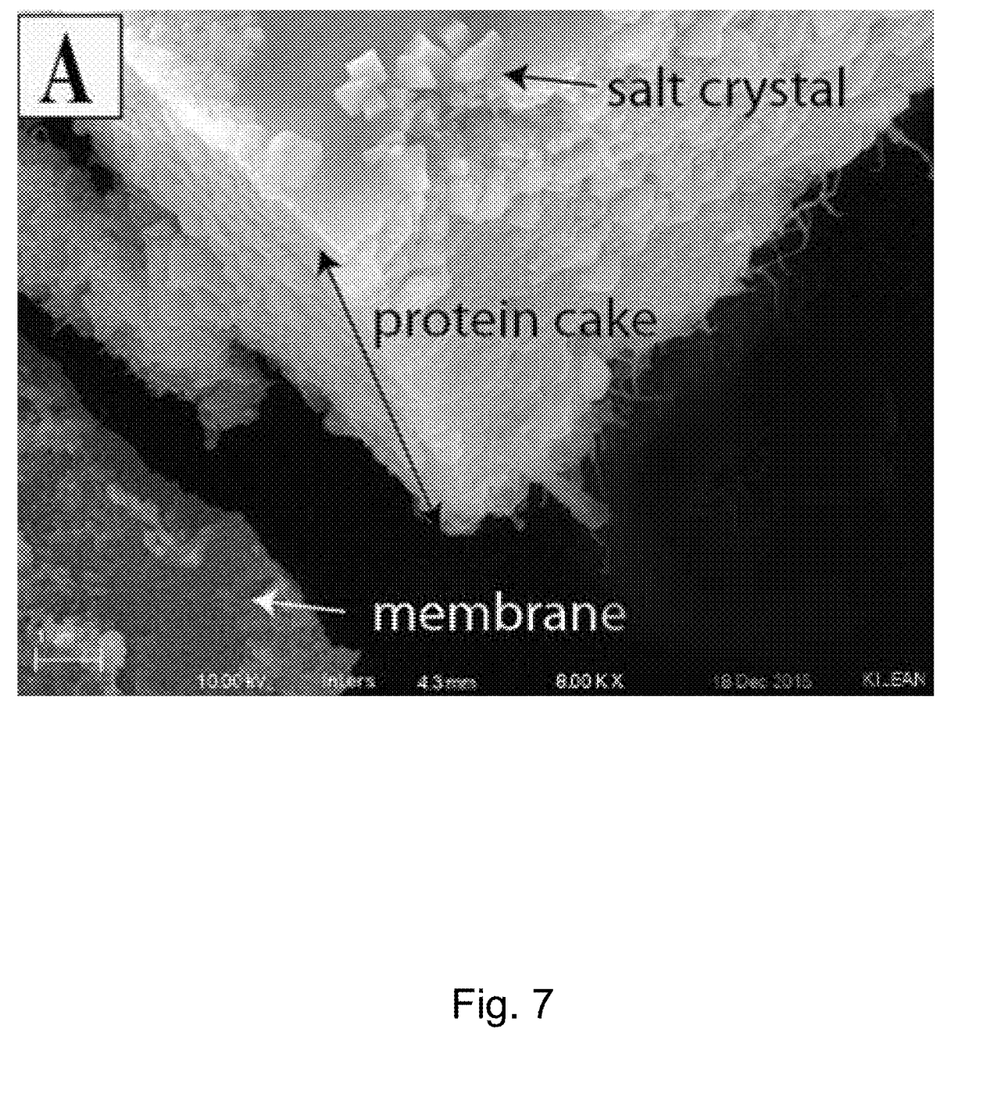
FIG. 7 shows dead end centrifugation of plasma with NPN membrane and resulting protein fouling.

FIG. 7 shows dead end centrifugation of plasma with a nanoporous silicon nitride membrane and resulting protein fouling. The resulting protein "cake" precludes separation of extracellular vesicles from the plasma, and dramatically illustrates why ultrafiltration and gelation methods are unable to purify exosomes from plasma without significant contamination from protein. The high permeability of ultrathin nanoporous silicon nitride membranes however, in a tangential flow configuration as described herein, remain clear of protein fouling and cake buildup. While not wishing to be bound to any particular theory, one hypothesis is that the high permeability of ultrathin nanoporous silicon nitride allows for enough transmembrane flow to pull exosomes into the pores of the nanoporous silicon nitride while in turn keeping the nanoporous silicon nitride membrane free of protein cake buildup.

Figure 8:
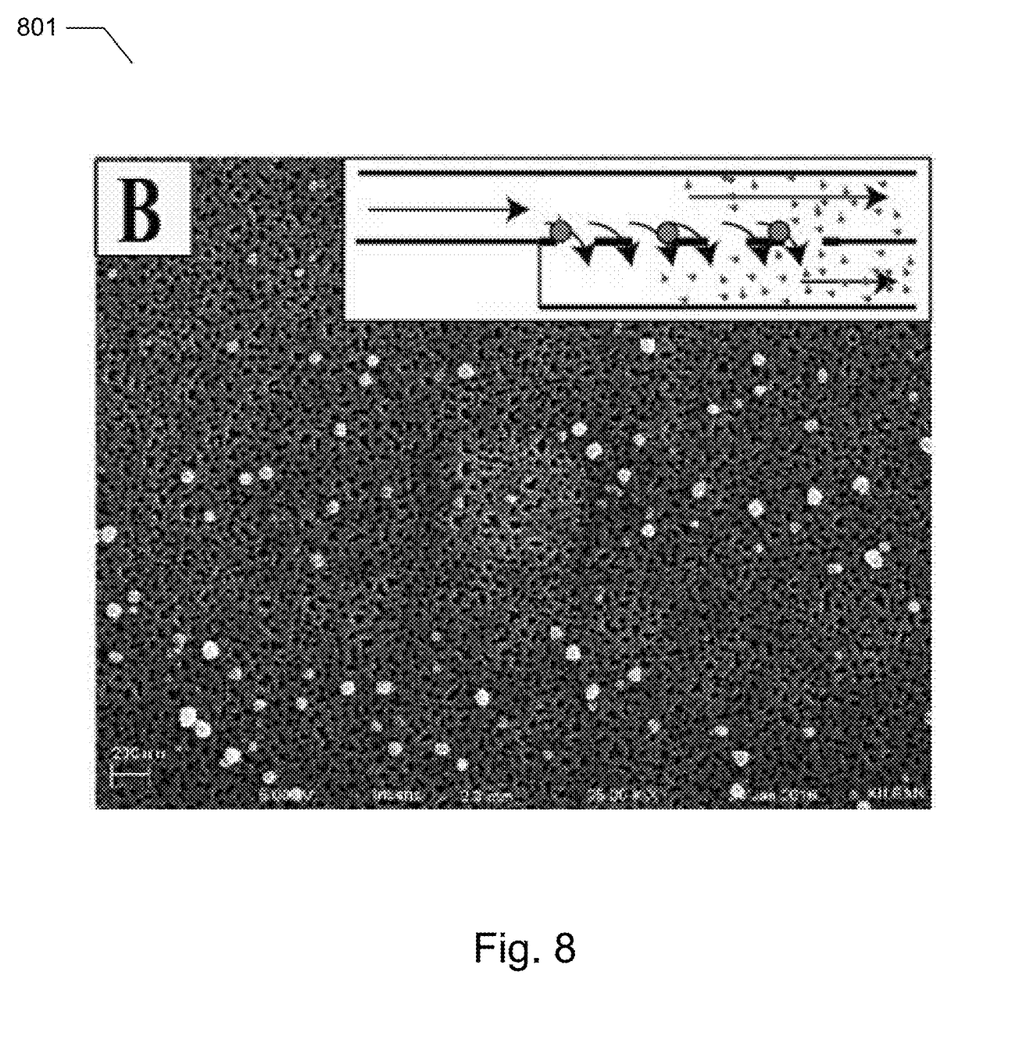
FIG. 8 depicts purification of exosomes using an NPN membrane in tangential flow mode.

FIG. 8 depicts purification of exosomes using a nanoporous silicon nitride membrane in tangential flow mode, as has been previously described herein. Note that the pores of the membrane are visible after passing undiluted plasma over the membrane indicating the absence of protein fouling with the present invention despite exposure to remarkably high protein levels. The bright 'glow' of the spherical particles is characteristic of organic materials on the inorganic nanoporous silicon nitride background. The distribution of vesicle sizes (20-100 nm) is also suggestive that these particles are exosomes.

In some embodiments of the present invention, various coatings and layers are applied to the nanoporous silicon nitride membrane. For example, very thin molecular layers with excellent hydrolytic stability may be employed. For example, a layer of 1-10 nanometer thickness. Such layers are designed so as not to occlude the pores or reduce permeability of the membrane. Such coatings provide enhanced surface interactions to assist in the capture of plasma components to supplement or otherwise interact with fluidic forces in the tangential flow device of the present invention.

An example of such a layer is that which is produced by functional carbene precursors to form uniform. Si—C and C—C attached monolayers on silicon, silicon nitride, and inert organic polymers under mild vacuum conditions. By utilizing meta-stable carbene species generated under mild UV-light illumination, the activation barrier for the Si—C and C—C bond formation is reduced and the variety of functional groups and surfaces that can be modified through surface-grafting reactions is expanded.

Ultrathin nanoporous silicon nitride (NPN) membranes can be functionalized with stable and functional organic molecules via carbene insertion chemistry. One example of a suitable organic coating for NPN is a thin, inert polymer layer that serves as the carbene attachment layer, and a stable polyethylene glycol (PEG) terminated monolayer that is linked to the polymer via non-hydrolytic C—C bonds generated by the vapor-phase carbene insertion. Such modifications to NPN provide the desired organic functionalities without significantly impacting pore size distribution or transport properties.

Coatings and monolayers for a substrate such as nanoporous silicon nitride (NPN) that may be employed with the present invention are described in U.S. patent application Ser. No. 15/130,208 to A. Shestopalov, L Xunzhi and J. L. McGrath filed on Apr. 15, 2016 and entitled "Methods for Depositing a Monolayer on a Substrate Field", the entire disclosure of which is incorporated herein by reference in it's entirety.

By defining surface chemistries, species capture from plasma can be controlled and selective capture of plasma components can be realized. Different chemical handles can be used to functionalize NPN membranes. Mixtures of different chemical handles can be used to further modulate the levels of adsorption of the plasma components and also to enhance adsorption selectivity. These chemical handles can be used in combination with different tangential flow regimes and membrane pore sizes to enhance specificity and selectivity of the membrane-plasma component interactions.

In the device of the present invention, there are three distinctive interfaces between the nanoporous silicon nitride (NPN) and blood plasma that act as non-binding, adsorbing, or selective surfaces for the selective removal of components such as extracellular vesicles. Individually these defined surfaces will (1) non-specifically limit adsorption of biomolecules from the plasma solution by creating water-like solvating environments near the interfaces (e.g., polyethylene glycol molecules or zwitterionic species), (2) non-selectively enhance adsorption of various biomolecules through ionic interactions and H-bonding (e.g., aminated interfaces), and (3) selectively bind serum components via specific biomolecular interaction (e.g., antigen-antibody interactions or specific H-bonding). Therefore, by creating homogeneously mixed monolayers that contain different ratios of non-binding, adsorbing, and selective species, capture selectivity can be established by the defined flow parameters and can further be enhanced by controlling the chemical composition of the membrane walls.

Defined surface chemistries may include, for example, antibodies that capture extracellular vesicles. Capture of extracellular vesicles by affinity using antibodies may include tangential flow arrangements such as those described and envisioned herein. In addition, antibodies may be combined with other defined surface chemistries for specific applications. There are also antibodies that are specific to extracellular vesicles. For example, CD63, CD9, CD81 and Hsp70 all have affinity to exosomes. The present invention and the various embodiments described, depicted and envisioned herein includes generically the employment of antibodies in general to capture, move, sort, retain, and otherwise process extracellular vesicles.

It is further stated that the various techniques, devices, methods and apparati described herein are also suitable for the capture of cell free DNA. Cell free fetal DNA for example provides a rich population of biomarkers using maternal blood sampling as a form of non-invasive prenatal diagnosis without the risk of procedure-related miscarriage.

The carbenylation approach can be used as a simple, robust and universal method to functionalize nanoporous materials with diverse classes of organic and biological species. The inventors have demonstrated that carbenylated monolayers on Si, Ge, SiN, ITO and polymers can be modified with various organic and biological molecules—small molecules, PEG-oligomers, GFP proteins and others—via simple surface reactions, and that they exhibit excellent hydrolytic stability in water and aqueous buffers for up to 2 weeks of exposure.

To form functional monolayers on nanoporous silicon nitride (NPN), the membranes will first be modified with an inert aliphatic coating that serves as a passivating layer and as a carbene attachment interface. Subsequently, the NHS-diazirine carbene precursors will be used to deposit the NHS-terminated monolayers on the aliphatic coating through the thermodynamically and hydrolytically stable C—C bonds. Lastly, individual or mixed NHS-terminated molecules (non-binding, adsorbing, and selective) will be reacted with the NHS-terminated monolayer to modify the resulting membranes with the desired chemical functionalities.

Figure 9:
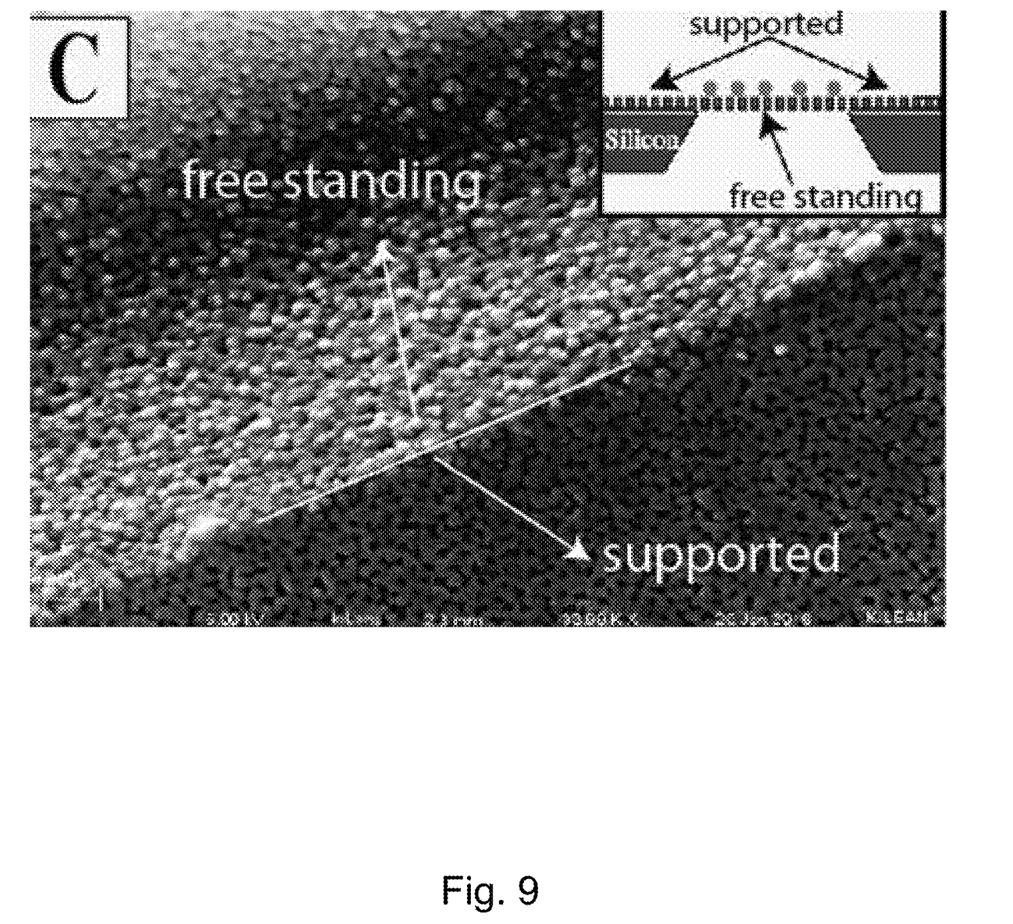
FIG. 9 depicts a supported membrane and associated exosome capture.

FIG. 9 is an image and associated diagram depicting a nanoporous silicon nitride membrane supported on the edges and with a free standing, permeable region that has captured exosomes while the supported, impermeable region has captured no exosomes. This image is another example of diffusion-driven physical sieving of extracellular vesicles that has been previously described and depicted herein.

Figure 10:
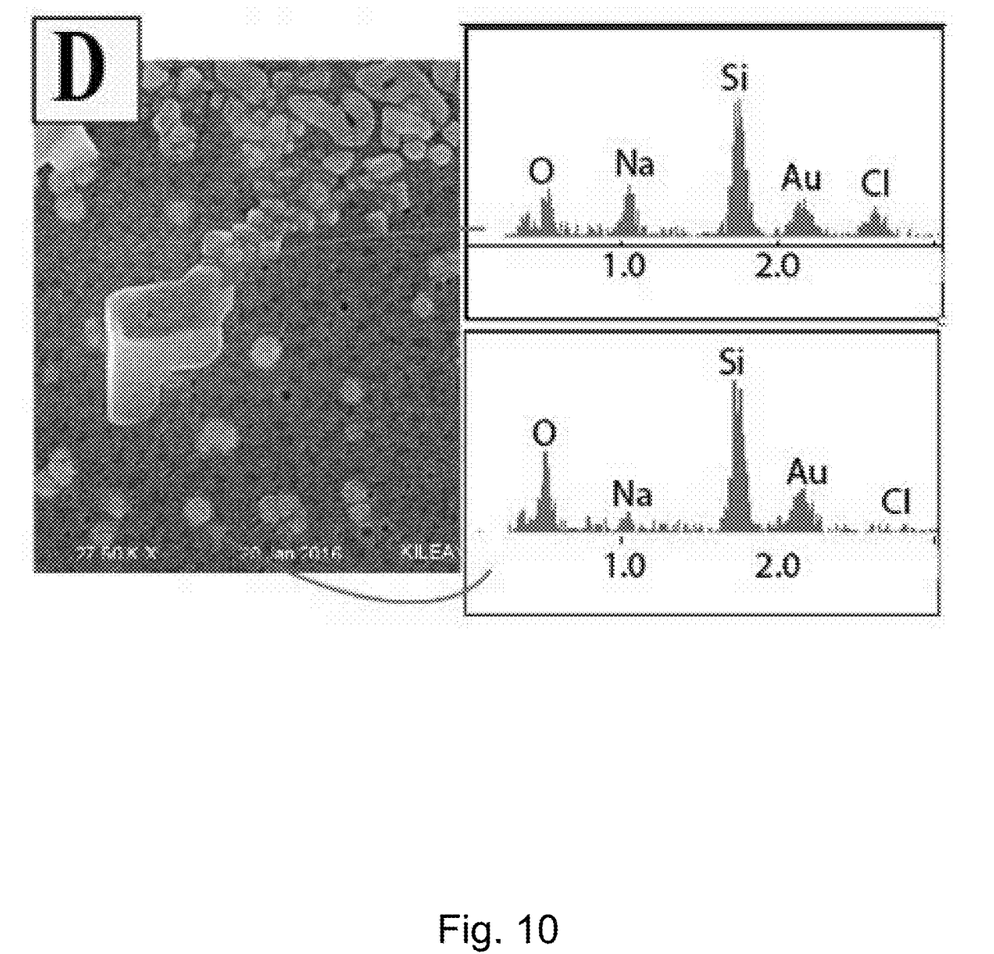
FIG. 10 depicts EDX chemical analysis of an in use membrane of the present invention.

FIG. 10 depicts EDX chemical analysis of an in use nanoporous silicon nitride membrane of the present invention. The region in the image shows where salt crystals and exosomes are both present. The chemical signature of the spherical particles depicted do not contain NaCl peaks, confirming that they are not salt crystals.

Membranes with 100-1,000 nanometer diameter pores are fabricated with patterning and etching methods. Specifically, 30 nanometer diameter pore membranes are fabricated using methods disclosed in PCT/US2014/1051316, the entire disclosure of which is incorporated herein by reference.

It can thus be seen that nanoporous silicon nitride membranes are compatible with processing of high protein content biofluids, such as undiluted plasma, without evidence of membrane fouling. It can also be seen that the capture of extracellular vesicles within the pores of nanoporous silicon nitride or similar membranes is a fast and elegant method for obtaining intact extracellular vesicles (such as exosomes) of very high purity. Further, the excess of nanoporous silicon nitride pores compared to the number of extracellular vesicles such as exosomes suggests that the present invention is able to capture nearly all exosomes in a biofluid sample.

A 30 nanometer pore size of nanoporous silicon nitride (NPN) membranes allows for the capture and retention of 30-100 nanometer extracellular vesicles such as exosomes, while passing contaminating species such as <30 nm proteins. In some embodiments of the present invention, larger pore sizes are desirable, and may include, for example, pore sizes as large as 120 nm. The large number of pores within our membranes (~$1.7 \times 10^8$ pores/mm$^2$ assuming 35 nm pores and 16% porosity) exceeds the number of exosomes in most biofluids by several orders of magnitude (assuming $10^5$ exosomes/mL for plasma). This exosome-to-NPN pore ratio suggests that nanoporous silicon nitride (NPN) membranes can capture nearly 100% of extracellular vesicles such as exosomes while leaving a large number of pores unoccupied to enable the removal of smaller contaminants.

Figure 11:
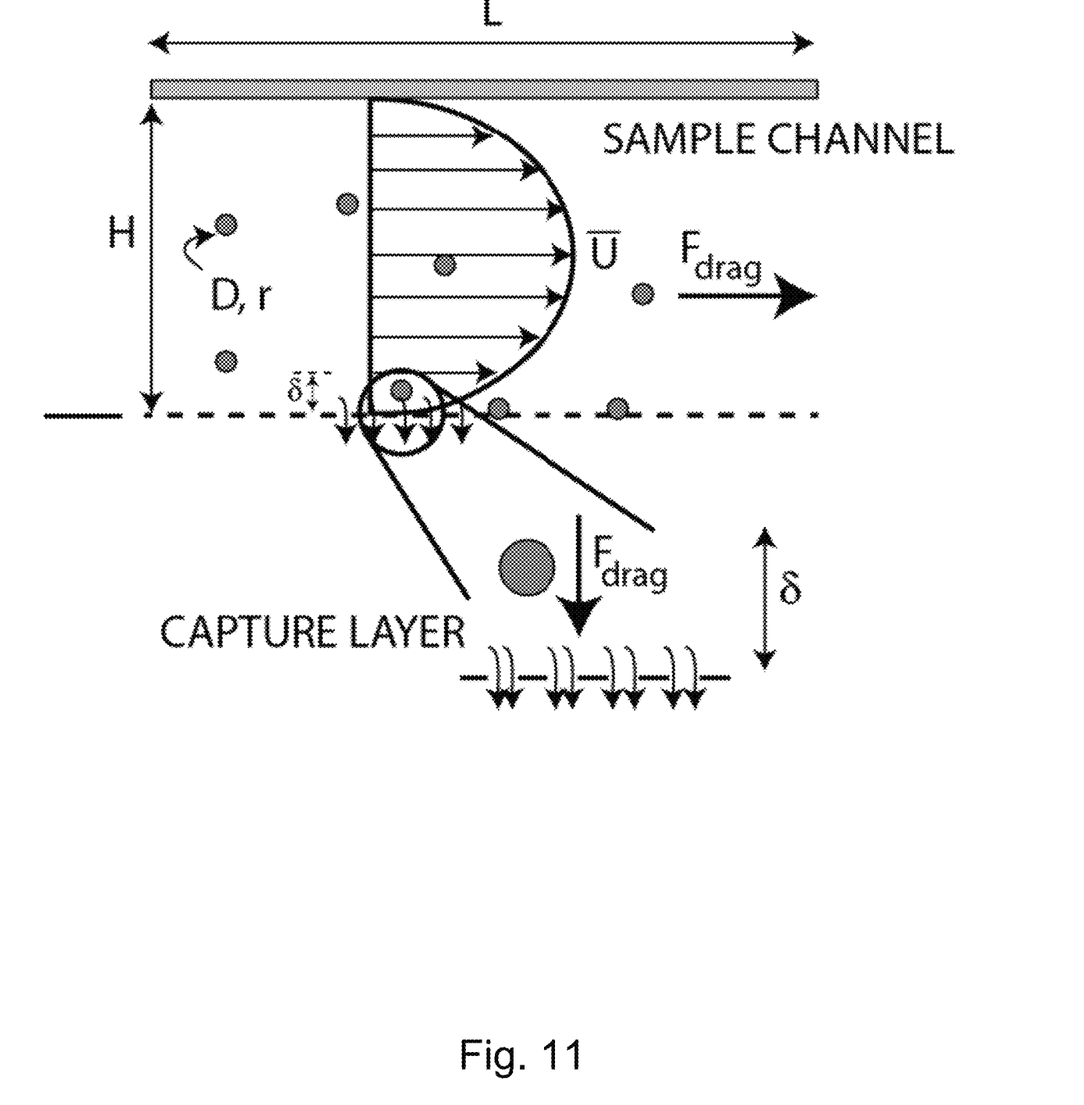
FIG. 11 is a diagram of fluid dynamics associated with exosome capture.

FIG. 11 is a diagram of fluid dynamics associated with exosome capture. The diagram depicts flow over a nanoporous silicon nitride membrane with exosomes represented as Brownian particles with diffusion coefficient D and radius r. A given sample channel (height H; length L) is predicted to contain parabolic flow through the bulk with a slight permeation of fluid through the membrane. Drag forces on the nanoparticles contained in the bulk will be largely tangential to the membrane, but very near the membrane they will be normal to the membrane as seen in FIG. 11. This region represents a capture layer with diffusion from the bulk into this capture layer being the key physical process that must be controlled by flow parameters.

Analytical techniques such as the creation of computational models for exosome capture can be used to determine the relationship between flow parameters and the capture of exosomes of various sizes. Computational models may be built with finite element analysis software that includes modeling of Brownian particles to the flow field. The models may, for example, include the hydraulic permeability of ultrathin membranes and assume a Newtonian fluid with the viscosity of plasma. In any resulting model, fluid streamlines in the top sample channel are expected to be parabolic with a slight permeation through the membrane into the lower chamber. The particles far from the channel will experience a large drag force tangential to the membrane while those very close to the membrane will experience drag toward the membrane from transmembrane convection and diminished tangential drag force. Exosomes entering this 'capture layer' will be pulled into the pore of the membrane and held there so long as there is transmembrane pressure.

A computational model may predict, for example, the height of the capture layer as a function of the flow parameters. It is expected that most well built computational models will indicate that the capture layer will be very small compared to the channel height.

$$\delta \ll H$$

Thus it is only through diffusive excursions from the bulk to the membrane that most exosomes will become trapped in the membrane pores, and we can expect a Peclet defined as $$Pe = \frac{\bar{U}/L}{D/H^2} = \frac{\bar{U}H^2}{LD}$$

To be a key predictor of exosome capture. Note that because the diffusion coefficient and the drag forces imparted by the fluid on a particle are both dependent on the friction factor f $$f = 6\pi\mu r$$

both will be dependent on the particle size r, and the probability of capture is expected to be strongly dependent on particle size. Use of such modeling will allow one to prescribe flow settings that tune the capture process to exosomes (or micro vessels) of a particular size. Use of such a model will allow determination of application specific dimensions to ensure complete capture of target particles (such as exosomes) from a flowable material in a single pass across the membrane of the present invention. Input pressures and channel dimensions are two such parameters. A computational model can also be used to prescribe pressures during the recovery process if simple 'backwashing' proves problematic in a given application and configuration. As previously described herein, defined surface chemistries may also be employed with the membrane of the present invention for specific applications or to improve the retention of desired material by the membrane, reject non-desired material, or remove the retained desired material when certain conditions (such as a pressure change) are applied.

What is claimed is:

1. A device for isolating extracellular vesicles from biofluids, the device comprising:
   a nanoporous membrane comprising a first surface with a plurality of pores;
   wherein the pores have a generally circular shape and a range of pore diameters between 20 nanometers and 120 nanometers and are configured to size selectively capture and retain the extracellular vesicles;
   a tangential fluid flow device for creating a tangential fluid flow velocity of a biofluid across the surface of the nanoporous membrane having a plurality of pores;
   a pressure gradient device in fluid communication with the biofluid wherein the pressure gradient device creates a pressure gradient through the nanoporous membrane;
   wherein the pressure gradient device is selected from the group consisting of a pump, a diaphragm, a vacuum device, a thermoelectric device, and a peltier device; and wherein the device for isolating extracellular vesicles from biofluids promotes blocking of the pores with extracellular vesicles to create an intentionally fouled nanoporous membrane.

2. The device of claim 1, further comprising a pressure gradient reversal device in communication with the pressure gradient device, wherein the pressure gradient reversal device is selected from the group consisting of a pump controller, a switch, a valve, a fluid diversion structure, and a vacuum controller.

3. The device of claim 1, wherein the nanoporous membrane is nanoporous silicon nitride.

4. The device of claim 1, wherein the density of pores of the nanoporous membrane is at least $10^7$ pores per square millimeter.

5. The device of claim 1, wherein the magnitude of the created tangential flow velocity is between 100 micrometers per second and 10 centimeters per second.

6. The device of claim 1, wherein the magnitude of the created pressure gradient through the nanoporous membrane is between 1 pascal and 1 atmosphere.

7. The device of claim 1, wherein the nanoporous membrane is configured as a channel having a channel length and a channel height for containing the tangential flow of a biofluid.

8. The device of claim 7, wherein the channel length along the principal direction of flow is between 1 millimeter and 1 meter.

9. The device of claim 7, wherein the channel height is between 100 nanometers and 1 millimeter.

10. The device of claim 1, wherein the nanoporous membrane further comprises a coating.

11. The device of claim 1, wherein the nanoporous membrane further comprises a defined surface chemistry.

12. The device of claim 1, wherein the nanoporous membrane further comprises a carbenylated monolayer.

13. The device of claim 1, wherein the nanoporous membrane further comprises an aliphatic coating.

14. The device of claim 1, wherein the nanoporous membrane further comprises polyethylene glycol.

15. The device of claim 1, wherein the nanoporous membrane further comprises a zwitterionic species.

16. The device of claim 1, wherein the nanoporous membrane further comprises an aminated interface.

17. The device of claim 1, wherein the nanoporous membrane further comprises a second surface having a plurality of pores extending therethrough; where the plurality of pores from the first surface extend through the second surface and where the plurality of pores of the first surface are of a greater diameter than the plurality of pores that extend through the second surface.

18. The device of claim 1, wherein the pores are tapered.

19. A device for isolating cell free DNA from biofluids, the device comprising:
   a nanoporous membrane comprising a surface with a plurality of pores;
   wherein the pores have a generally circular shape and a range of pore diameters between 20 nanometers and 120 nanometers and are configured to size selectively capture and retain the cell free DNA;
   a tangential fluid flow device for creating a tangential fluid flow velocity of a biofluid across the surface of the nanoporous membrane having a plurality of pores;
   a pressure gradient device in fluid communication with the biofluid wherein the pressure gradient device creates a pressure gradient through the nanoporous membrane;
   wherein the pressure gradient device is selected from the group consisting of a pump, a diaphragm, a vacuum device, a thermoelectric device, and a peltier device; and wherein the device for isolating cell free DNA from biofluids promotes blocking of the pores with cell free DNA to create an intentionally fouled nanoporous membrane.

20. The device of claim 19, further comprising a pressure gradient reversal device in communication with the pressure gradient device, wherein the pressure gradient reversal device is selected device is selected from the group consisting of a pump controller, a switch, a valve, a fluid diversion structure, and a vacuum controller.

21. The device of claim 19, wherein the nanoporous membrane is nanoporous silicon nitride.

22. The device of claim 19, wherein the density of pores of the nanoporous membrane is at least $10^7$ pores per square millimeter.

23. The device of claim 19, wherein the magnitude of the created tangential flow velocity is between 100 micrometers per second and 10 centimeters per second.

24. The device of claim 19, wherein the magnitude of the created pressure gradient through the nanoporous membrane is between 1 pascal and 1 atmosphere.

25. The device of claim 19, wherein the nanoporous membrane is configured as a channel having a channel length and a channel height for containing tangential flow of a biofluid.

26. The device of claim 25, wherein the channel length along the principal direction of flow is between 1 millimeter and 1 meter.

27. The device of claim 25, wherein the channel height is between 100 nanometers and 1 millimeter.

28. The device of claim 19, wherein the nanoporous membrane further comprises a coating.

29. The device of claim 19, wherein the nanoporous membrane further comprises a defined surface chemistry.

30. The device of claim 19, wherein the nanoporous membrane further comprises a carbenylated monolayer.

31. The device of claim 19, wherein the nanoporous membrane further comprises an aliphatic coating.

32. The device of claim 19, wherein the nanoporous membrane further comprises polyethylene glycol.

33. The device of claim 19, wherein the nanoporous membrane further comprises a zwitterionic species.

34. The device of claim 19, wherein the nanoporous membrane further comprises an aminated interface.

35. The device of claim 19, wherein the pores are tapered.

* * * * *

UNITED STATES PATENT AND TRADEMARK OFFICE
CERTIFICATE OF CORRECTION

PATENT NO. : 11,959,841 B2
APPLICATION NO. : 16/476329
DATED : April 16, 2024
INVENTOR(S) : McGrath et al.

It is certified that error appears in the above-identified patent and that said Letters Patent is hereby corrected as shown below:

In the Claims

Column 10, Line 17, Claim 7, 'the tangential flow of a' should read -the tangential flow of the- Column 11, Line 4, Claim 20, 'device is selected device is selected from the group' should read -device is selected from the group- Column 11, Line 20, Claim 25, 'for containing tangential flow of' should read -for containing the tangential flow of- Signed and Sealed this
Third Day of September, 2024

Katherine Kelly Vidal
*Director of the United States Patent and Trademark Office*